US006428974B1

(12) United States Patent
Nakano et al.

(10) Patent No.: US 6,428,974 B1
(45) Date of Patent: Aug. 6, 2002

(54) MICROPLATE FOR DRUG SUSCEPTIBILITY TESTING CONTAINING A DRUG, A COLOR REAGENT, AND COLOR SUPPRESSANT

(75) Inventors: Tomota Nakano; Toshihiro Ono, both of Isehara (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/859,213

(22) Filed: May 16, 2001

Related U.S. Application Data

(63) Continuation-in-part of application No. 09/277,247, filed on Mar. 26, 1999, now abandoned.

(30) Foreign Application Priority Data

Apr. 3, 1998 (JP) .......................................... 10-107168

(51) Int. Cl.$^7$ ................................................ C12Q 1/18
(52) U.S. Cl. ................... 435/32; 435/287.9; 435/288.4; 435/963
(58) Field of Search ............................. 435/32, 25, 29, 435/254.22, 287.9, 288.4, 963

(56) References Cited

U.S. PATENT DOCUMENTS

| | | | | |
|---|---|---|---|---|
| 4,975,367 A | * | 12/1990 | Albarella et al. | 435/11 |
| 5,192,663 A | | 3/1993 | Sinor et al. | 435/7.25 |
| 5,334,508 A | * | 8/1994 | Hoenes | 435/25 |
| 5,686,110 A | | 11/1997 | Greenwald et al. | 424/486 |
| 5,909,114 A | | 6/1999 | Uchiyama et al. | 324/94 |
| 6,046,021 A | * | 4/2000 | Bochner | 435/324 |

FOREIGN PATENT DOCUMENTS

JP 9-127097 5/1997

OTHER PUBLICATIONS

Pfaller M. Multisite Reproducibility of Colorimetric Broth Microdilution Method for Antifungal Susceptibility Testing of Yeast Isolates. J of Clinical Microbiology 32(7) 1625–1628, Jul. 1994.*
Journal of the Japanese Society for Clinical Microbiology. 7(4)73, 1997.*
Reference Method for Broth Dilution Antifungal Susceptibility Testing of Yeasts; Proposed Standards (M27–P), NCCLS, vol. 12, No. 25 (1992).
Reference Method for Broth Dilution Antifungal Susceptibility Testing of Yeasts; Proposed Standards (M27–A), NCCLS, vol. 17, No. 9 (1997).
Pfaller, M.A. et al., J. Clin. Microbiol. 32: 506–509, 1994.
Pfaller, M.A. et al., J. Clin. Microbiol. 32: 1626–1628, 1994.
Yamane et al., Rinsyo Byori, 44: 67–75, 1996.
Japanese Journal of Medical Mycology Society, 36, 61–86, 1995 (abridged English language translation).
Mosman, TJ, Immunol. Methods, 65, 55–63, 1983.
9th Japanese Society for Clinical Microbiology, Jan.31–Feb. 1, 1998 (abridged English language translation).
Ishiyama, M. et al., Talanta, 44, 1299–1305, 1997.
Reference Method for Broth Dilution Antifungal Susceptibility Testing of Yeasts; Approved Standard (M27–A), NCCLS, vol. 17, No. 9 (1997).
John N. Galgani et al., "Reference Method For Broth Dilution Antifungal Susceptibility Testing of Yeast: Tentative Standard", (Oct. 1995) NCCLS, M27–T, vol. 15, No. 10.

* cited by examiner

Primary Examiner—Ralph Gitomer
(74) Attorney, Agent, or Firm—Darby & Darby

(57) ABSTRACT

A reagent for a drug susceptibility testing which is simple and highly reproducible is provided. A microplate for a drug susceptibility testing wherein a drug and a color reagent containing a tetrazolium salt, 1-methoxy-5-methylphenazinium methylsulfate (1-methoxy PMS), potassium ferricyanide and potassium ferrocyanide are formed into a solid phase on the microplate by a vacuum drying, and a kit consisting of the microplate and a medium for a cell growth, and the testing method.

4 Claims, 1 Drawing Sheet

Figure 1:
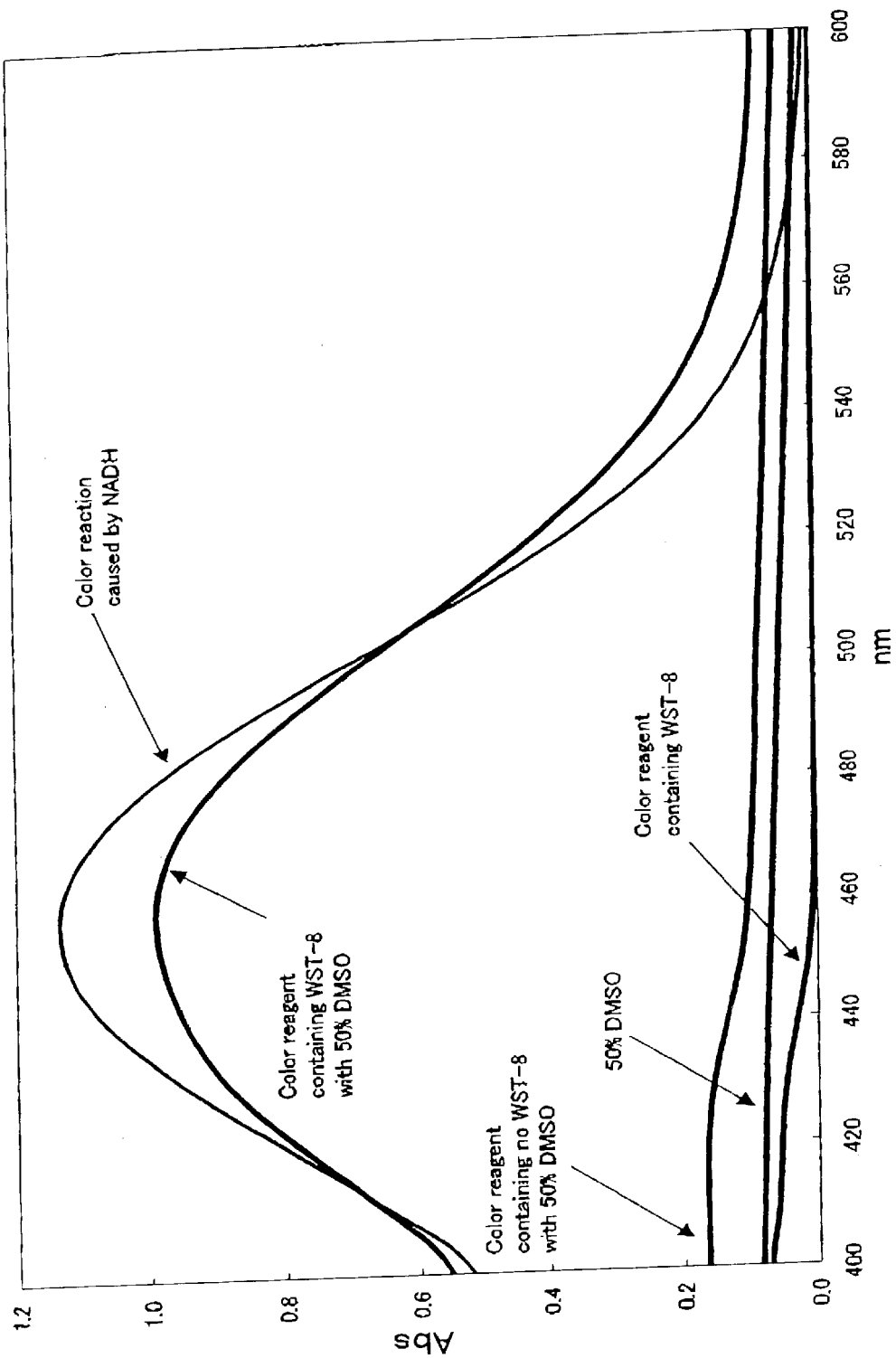

MICROPLATE FOR DRUG SUSCEPTIBILITY TESTING CONTAINING A DRUG, A COLOR REAGENT, AND COLOR SUPPRESSANT

This application is a CIP of U.S. application Ser. No. 09/277,247, filed Mar. 26, 1999, now abandon.

BACKGROUND OF THE INVENTION

The invention relates to a microplate, kit and testing method for a susceptibility testing of antibacterial drugs, especially antifungals.

With the increase of a crisis frequency of deep mycosis due to a yeast-like fungus and the diversification of casual bacteria, and the appearance of a bacterial strain showing the resistance to antifungal agents, an therapeutic drug appropriate for the infection disease is indispensable, and thus the necessity of a susceptibility testing of antifungal drugs has increased in medical services. As for the sensitivity testing method of yeast-like fungi, in 1992 Re Reference Method for Broth Dilution Antifungal Susceptibility Testing of Yeasts; Proposed Standards (M27-P), and in 1995 Tentative Standard (M27-T) were reported by the National Committee for Clinical Laboratory Standards (NCCLS) in United States, and Approved Standards (M27-A) was recommended in June, 1997. The M27-A method is a microdilution method in 0.2 ml of the medium amount, and is a method in which the bacterial growth inhibition concentration is read by a visual observation on the turbidity of a bacterial growth end point associated with the bacterial growth usually after the incubatation in the air for 46–50 hrs.

On the other hand, in Japan an independently improved microdilution method based on the above M27-P method was reported by the Standardization Committee in Japanese Society of Medical Mycology (Yamaguchi et al., Japanese Journal of Medical Mycology Society, 36; 61–86, 1995).

However, the NCCLS M27-A and Japanese Society for Medical Mmycology methods contain the following problems in case of an operation in clinical examination services.

1) It takes time for the preparation and the separate infusion. 2) It is difficult to read the bacterial growth end point (80% bacterial growth inhibition) in an azole type drug by the naked eye, and reading the bacterial growth end point requires to be fully accustomed. 3) In case of reading byamicroplate reader, it is difficult for packets to disperse uniformly, and it happens to read even a minute packet, consequently resulting to a reason for the decrease of reliability, etc.

Owing to these, in clinical examination services a testing method which can be carried out by a simpler operation than those reported currently and easily give a reliable reading result, and the reagent development for it are waited. It maybe considered that a reagent favorable for aperson carrying out the testing has a property in which the drug susceptibility testing can be started only by separately inoculating a bacterial suspension of a sample onto a microplate and the bacterial growth end point can easily be read after incubating this for a certain time. However, the bacterial growth end point that is read is required not to largely depart from that by the NCCLS M-27 method.

It can be considered that the development of a microplate in which a testing reagent is previously made into concentration dilution series contributes to the simplification of a drug susceptibility testing. However, owing to the fact that the bacterial growth end point is read from the degree of the turbidity in case of separately infusing a bacterial suspension of a sample onto said microplate, the above problem at the time of reading remains without any solution. As a reading method of the bacterial growth end point without depending on the turbidity, by using (Alamar Biosciences Inc., Sacramento, Calif.), a redox indicator, the method to read from the change of color-tone in the medium (Pfaller, M. A. et. al., J. Clin. Microbiol. 32: 506–509, 1994; Pfaller, M. A. et. al., J. Clin. Microbiol. 32: 1625–1628, 1994) and the method to read by using resazurin as an indicator (Yamane et. al., Rinsyo Byori (in Japanese), 44; 67–75, 1996) are reported. However, in these methods the procedure of adding the indicators to the culture liquid or the bacterial culture liquid is necessary. Further, these method become difficult for reading in the case that the medium shows an intermediate color, and additionally there is the handling problem that the medium mixed with resazurin must be stored and incubated under dark owing to the instability to light (JP, A, H9-127097).

The inventors applied the method of reducing the tetrazolium salt and measuring the amount of formazan (color) thus resulted (Formazan color method: Mosmann, T., J. Immunol. Methods, 65, 55–63, 1983) to the measurement of the growth rate of yeast-like fungi, and found that there was a correlation between the absorbancy and the turbidity (9th. Japanese Society for Clinical Microbiology Meeting: Jan. 31–Feb. 1, 1998). Then, the inventors tried to develop a simple determining agent, i.e. an agent with which the drug susceptibility testing could be started only by separately infusing a fungal suspension of a sample onto a microplate, and which could easily determine a fungal growth end point after incubating it for a certain period of time, by applying the above-mentioned method of measuring into a drug susceptibility testing. Specifically, the inventors produced a microplate wherein the drug and the color reagent were premixed in wells of the microplate and the mixed reagents were formed into a solid phase by a vacuum drying. However, in the step of drying, formazan was formed in wells of the microplate and the microplate could not be used for a drug susceptibility testing since the formazan caused experimental errors. Therefore, a microplate wherein both a drug and a color reagent were formed into a solid phase could not appropriately be produced.

SUMMARY OF THE INVENTION

However, as a result of further investigation to develop the above-mentioned simple determining agent, the inventors found that the formation of formazan in the step of drying is caused by a reaction of a color reagent with dimethyl sulfoxide (DMSO) in a drug solution, which is concentrated during the step of drying. Further, the inventors found that a microplate wherein both a drug and a color reagent can be formed into a solid phase without the formation of formazan by following steps: (1) separately infusing a drug solved with DMSO or a DMSO contained solution into wells of a microplate, (2) evaporating DMSO from the wells by drying under reduced pressure, (3) adding a color reagent into the wells, and (4) drying under reduced pressure again. Finally, the inventors confirmed that a drug susceptibility testing can easily be carried out by using the microplate produced without formation of formazan and the present invention has been completed. Further, the inventors found that the color reaction due to medium components can be suppressed by concurrently forming potassium ferricyanide and potassium ferrocyanide into a solid phase.

Namely, the invention is to provide a microplate for a drug susceptibility testing wherein a drug and a color reagent are formed into a solid phase on the microplate by twice vacuum drying steps. Preferably, the microplate is substantially free of formazan. According to a more preferred embodiment, the microplate is free of formazan.

Also, the invention is to provide a microplate for a drug susceptibility testing wherein the above color reagent contains a tetrazolium salt, 1-methoxy-5-methylphenazinium methylsulfate (hereafter described as 1-methoxy PMS), potassium ferricyanide and potassium ferrocyanide, and a kit product consisting of the microplate and a medium for a cell growth.

Further, the invention is to provide a drug susceptibility testing method comprising the following steps.

(1) Preparing a microplate wherein a drug and a reagent which contains a tetrazolium salt, 1-methoxy-5-methylphenazinium methylsulfate, potassium ferricyanide and potassium ferrocyanide are formed into a solid phase on the microplate by twice vacuum drying steps;

(2) adding a sample containing cells to the above microplate;

(3) incubating the above microplate; and (4) reading the growth rate of the cells by the coloration rate.

In the following, the invention will be explained in detail.

The preparation of the microplate of the invention and the drug susceptibility testing method by its use were carried out by the method described in the following.

A. Preparation Method for Microplate with Drug and Color Reagent Formed into Solid Phase For the solid phase formation on a microplate, a drug solution is dissolved in dimethyl sulfoxide (DMSO). By the use of the prepared drug a two fold dilution series is prepared in an appropriate concentration range with DMSO or a distilled sterile water, and a fixed amount is separately infused into each well and formed into the dry and solid phase under vacuum for 24 hrs. As the concentration range of a drug formed into the solid phase are cited a range such as, for example, Amphotericine B (AMPH): 16–0.03 μg/ml, Flucytosine (5-FC): 64–0.125 μg/ml, Fluconazole (FLCZ): 64–0.125 μg/ml, Miconazole (MCZ): 32–0.06 μg/ml and Itraconazole (ITCZ): 16–0.03 μg/ml. After finishing the solid phase formation of a drug, the color reagent (containing a tetrazolium salt, 1-methoxy PMS, potassium ferricyanide and potassium ferrocyanide) is separately infused into each well and formed into a solid phase by a vacuum drying. The known tetrazolium salts showing a color by the reduction of the tetrazolium salts can be used, though appropriately is used a tetrazolium salt in which favorably the formed formazan pigment is easily soluble in water and the cell toxicity is low, for example, 4-[3-(2-methoxy-4-nitrophenyl)-2(4-nitrophenyl)-2H-5-tetr azolino]-1,3-benzene disulfonate sodium salt (WST-8; manufactured by Dojindo Laboratories, Ishiyama, M. et., al., Talanta, 44: 1299–1305, 1997). The prepared plate can be stored at 4° C.

B. Antifungal Susceptibility Testing by using Plate with Solid Phase Formation of Drug 1) Medium A medium for testing is prepared as follows. RPMI 1640 powder medium (with L-gulutamic acid, without NaHCO$_3$, without phenol red) 10.4 g, glucose 10.0 g, NaHCO$_3$ 2.0 g and morpholinopropanesulfonic acid (MOPS) 34.53 g are added to a pure water 800 ml, and dissolved. The solution is adjusted to pH 7.0 by 1N NaOH. The total volume of the solution is adjusted to 1000 ml and the solution is sterilized by filtration. The medium thus prepared can be stored at 4° C.

2) Fungal Strain

As a fungal strain for the application of the method are cited *Candida genera* such as *Candida albicans, Candida parapsilosis, Candida tropicalis* and *Candida glabrata*, and their relative yeast fungi, and especially a fungal strain which grows sufficiently in Sabourand-dextrose agar medium at 35° C. for 24 hrs. is made the object.

As a fungal strain for an accuracy control are used *Candida albicans* ATCC 90028, *Candida albicans* ATCC 24433, *Candida parapsilosis* ATCC 90018, *Candida parapsilosis* ATCC 22019, *Candida tropicalis* ATCC 750, *Candida krusei* ATCC 6258, etc.

3) Testing method

The trace suspension dilution method of the invention is carried out as follows.

(1) A colony of a fresh isolate grown in an agar medium is used. Further, in case of using a stock strain the pre-incubation is done two times in an agar medium, followed by the usage. (2) A fungal suspension of the McFarland # 0.5 tubidity is prepared by the use of the fungal colony.

(2)-1. Three to five fungal colonies are inoculated in a test tube poured with a sterile saline 5 ml, and suspended. After suspending the suspension is thoroughly stirred by a vortex mixer so that it becomes homogeneous. The sterile saline is prepared by dissolving NaCl 8.5 g in the pure water 1000 ml and sterilizing in an autoclave (121° C., 15 min.).

(2)-2. The fungal suspension is adjusted to the turbidity corresponding to McFarland # 0.5.

(3) The fungal suspension prepared in (2) is taken by a micropipete, added to the medium for the testing, thoroughly stirred by a vortex mixer and diluted so that the fixed concentration is obtained.

(4) The fungal suspension prepared in (3) is separately inoculated in a fixed: amount into a well in which a drug and a color reagent are formed into a solid phase. The replication of the fungal suspension is done within 15 min. after the fungal suspension preparation (in the case that the inoculation can not be done, it can be stored at 4° C. within 2 hrs.). At the same time, as a negative control it is made that the medium for the testing is separately infused in a fixed amount into a well in which only a color reagent is formed into a solid phase, and as a positive control it is made that the fungal suspension prepared in (3) is separately infused in a fixed amount into a well in which only a color reagent is formed into a solid phase.

(5) After lidding the plate an aerobic culture is done at 35±1° C.

4) Reading method

The reading is carried out by the measurement values at a 24 or 48 hrs. incubation.

After stirring the microplate for 1 min., the absorbancy of the dominant wave length 450 nm and the complementary wave length 630 nm is measured, and the reading is carried out by the following method.

1. The minimum concentration showing the absorbency in the complete growth inhibition equal to or less than that in the negative control is made the minimum growth inhibition concentration (MIC).

2. The drug concentration of a well showing the absorbency equal to or less than the 80% growth inhibition concentration (IC 80) obtained by the following equation is made MIC.

$$IC80 = (\text{positive control} - \text{negative control}) \times 0.2 + \text{negative control}$$

C. Composition of Kit

In the kit of the invention are included a microplate prepared by the vacuum drying method as described above in which a drug and a color reagent are formed into a solid phase, and a medium for the testing. Namely, as an example of the kit of the invention is cited an antifungal susceptibility testing kit containing a microplate in which an appropriate antifungal such as AMPH, 5-FC, FLCZ, MCZ or ITCZ, and a color reagent are formed into a solid phase, and as a medium for the testing are cited glucose of 1.2%, MOPS buffered PRMI 1640 medium, and a sterile saline.

In the following, Example 1 shows that formazan was not formed in wells of the microplate by the method of the invention. Further, the invention will be explained in more detail by showing the Example 2 of the present invention and the turbidity method (the proposed method of Japanese Society for Medical Mycology) for the comparison. Further, the invention is not limited by the below examples and is susceptible of modification without departing from the spirit of the invention.

EXAMPLES

Example 1

A. Testing Method 1) 0.05 mL of 0 to 100% DMSO solution is mixed with 0.05 mL of a color reagent (0.28 mM 4-[3-(2-methoxy-4-nitrophenyl)-2-(4-nitrophenyl)-2H-5-terazolio]-1,3-benzene disulfonate sodium salt (WST-8); 1.4 $\mu$M 1-methoxy PMS; 0.2 mM potassium ferricyanide; 0.2 mM potassium ferrocyanide) in each well of a microplate. The microplate is incubated at 25° C. and the absorbency of the dominant wave length 450 nm and the complementary wave length 630 nm is measured at every constant time. In parallel, as negative control in which formazan is not formed, the DMSO solution is mixed with the color reagent without WST-8 and the absorbancy under no formazan condition is measured.

2) 2mL of purified water or DMSO is mixed with 2 mL of a color reagent (0.35 mM WST-8; 1.75 $\mu$M 1-methoxy PMS; 0.25 mM potassium ferricyanide; 0.25 mM potassium ferrocyanide) and the obtained solution is incubated at 25° C. Then, the absorption spectrum is measured. In parallel, as negative control in which formazan is not formed, purified water or DMSO is mixed with the color reagent without WST-8 and the absorption spectrum under no formazan condition is measured. Further, 2 mL of 0.1 mM $\beta$-Nicotinamide-adenine dinucleotide, reduced form ($\beta$-NADH) is mixed with 2 mL of the color reagent and the absorption spectrum of WST-8 formazan is measured.

B. Results

In the wells in which the concentration of DMSO is 35% or more, the absorbency is increasing as time advances and the absorbency is increasing as the concentration of DMSO increases. On the other hand, in the wells in which the concentration of DMSO is less than 30% and the wells in which the color reagent without WST-8 is added, the absorbancy is not increasing. The results are shown in Table 1.

TABLE 1

Coloring of a color reagent caused by DMSO

| Color reagent | Concentration of DMSO in wells (%) | Time after mixing | | | | | | |
|---|---|---|---|---|---|---|---|---|
| | | 5 min | 30 min | 1 hr | 2 hrs | 3 hrs | 4 hrs | 5 hrs |
| With WST-8 | 50 | 0.194 | 0.274 | 0.311 | 0.349 | 0.375 | 0.391 | 0.401 |
| | 47.5 | 0.125 | 0.194 | 0.230 | 0.273 | 0.300 | 0.323 | 0.336 |
| | 45 | 0.060 | 0.107 | 0.140 | 0.181 | 0.211 | 0.237 | 0.252 |
| | 42.5 | 0.032 | 0.055 | 0.078 | 0.108 | 0.137 | 0.159 | 0.174 |
| | 40 | 0.017 | 0.026 | 0.036 | 0.054 | 0.069 | 0.088 | 0.099 |
| | 35 | 0.009 | 0.011 | 0.013 | 0.016 | 0.020 | 0.029 | 0.030 |
| | 30 | 0.008 | 0.009 | 0.008 | 0.007 | 0.009 | 0.014 | 0.013 |
| | 20 | 0.009 | 0.007 | 0.005 | 0.010 | 0.007 | 0.009 | 0.008 |
| | 10 | 0.005 | 0.008 | 0.006 | 0.008 | 0.007 | 0.009 | 0.007 |
| | 0 | 0.007 | 0.006 | 0.005 | 0.008 | 0.006 | 0.009 | 0.007 |
| Without WST-8 | 50 | 0.013 | 0.015 | 0.012 | 0.009 | 0.006 | 0.010 | 0.008 |

As a result of measuring the absorption spectrum, in the mixed solutions in which the absorbancy is increasing, a peak caused by WST-8 formazan is shown in the vicinity of 460 nm as well as in the solution in which the color reagent containing WST-8 is reduced by $\beta$-NADH. The results are shown in Table 2 and FIG. 1.

TABLE 2

The result of measuring the absorption spectrum

| Wave length (nm) | Color reagent containing WST-8 with 50% DMSO | Color reagent containing no WST-8 with 50% DMSO | 50% DMSO | Color reagent with WST-8 | Color reaction caused by NADH |
|---|---|---|---|---|---|
| 600 | 0.0859 | 0.0540 | 0.0232 | 0.0007 | 0.0112 |
| 590 | 0.0890 | 0.0569 | 0.0259 | 0.0009 | 0.0165 |
| 580 | 0.0973 | 0.0606 | 0.0289 | 0.0010 | 0.0254 |
| 570 | 0.1120 | 0.0630 | 0.0315 | 0.0012 | 0.0392 |
| 560 | 0.1356 | 0.0662 | 0.0340 | 0.0012 | 0.0615 |
| 550 | 0.1728 | 0.0686 | 0.0369 | 0.0013 | 0.0978 |
| 540 | 0.2293 | 0.0719 | 0.0396 | 0.0015 | 0.1557 |
| 530 | 0.3100 | 0.0747 | 0.0430 | 0.0019 | 0.2446 |
| 520 | 0.4165 | 0.0784 | 0.0466 | 0.0019 | 0.3691 |
| 510 | 0.5433 | 0.0822 | 0.0501 | 0.0018 | 0.5252 |
| 500 | 0.6775 | 0.0862 | 0.0535 | 0.0018 | 0.6974 |
| 490 | 0.8016 | 0.0884 | 0.0566 | 0.0019 | 0.8628 |
| 480 | 0.9011 | 0.0913 | 0.0601 | 0.0020 | 1.0000 |
| 470 | 0.9656 | 0.0960 | 0.0635 | 0.0026 | 1.0940 |
| 468 | 0.9739 | 0.0969 | 0.0642 | 0.0029 | 1.1068 |
| 466 | 0.9804 | 0.0978 | 0.0649 | 0.0032 | 1.1173 |
| 464 | 0.9851 | 0.0989 | 0.0655 | 0.0037 | 1.1254 |
| 462 | 0.9884 | 0.1001 | 0.0662 | 0.0043 | 1.1315 |
| 460 | 0.9898 | 0.1015 | 0.0667 | 0.0051 | 1.1344 |

TABLE 2-continued

The result of measuring the absorption spectrum

| Wave length (nm) | Color reagent containing WST-8 with 50% DMSO | Color reagent containing no WST-8 with 50% DMSO | 50% DMSO | Color reagent with WST-8 | Color reaction caused by NADH |
|---|---|---|---|---|---|
| 458 | 0.9899 | 0.1031 | 0.0672 | 0.0062 | 1.1351 |
| 456 | 0.9886 | 0.1049 | 0.0678 | 0.0074 | 1.1338 |
| 454 | 0.9861 | 0.1070 | 0.0685 | 0.0089 | 1.1307 |
| 452 | 0.9825 | 0.1094 | 0.0693 | 0.0106 | 1.1257 |
| 450 | 0.9778 | 0.1124 | 0.0701 | 0.0128 | 1.1187 |
| 440 | 0.9401 | 0.1324 | 0.0740 | 0.0287 | 1.0493 |
| 430 | 0.8746 | 0.1535 | 0.0766 | 0.0463 | 0.9332 |
| 420 | 0.7693 | 0.1636 | 0.0793 | 0.0553 | 0.7895 |
| 410 | 0.6475 | 0.1643 | 0.0818 | 0.0602 | 0.6400 |
| 400 | 0.5517 | 0.1632 | 0.0839 | 0.0712 | 0.5186 |

Considering from the results so far obtained, it is believed that formazan is formed since DMSO reduces WST-8 as a terazolium salt.

Example 2

A. Used Fungal Strain

For the accuracy control were used 6 fungal strains wherein the MIC allowance range was described in the NCCLS M27-A: *Candida albicans* ATCC 90028, *Candida albicans* ATCC 24433, *Candida parapsilosis* ATCC 22019, *Candida parapsilosis* ATCC 90018, *Candida tropicalis* ATCC 750, and *Candida krusei* ATCC 6258.

Every fungal strain was subcultured two times in the Sabourand-dextrose agar medium, and subsequently the testing was carried out by using the fungal colony within 24 hrs. in the incubation.

B. Microplate for Testing

Four drugs of AMPH, 5-FC, FLCZ and MCZ were considered. The drug solution for the solid phase formation on the microplate was prepared as follows. The drug was dissolved in dimethylsulfoxide (DMSO) or diluted by using it. The solution was prepared so that it was AMPH 128 µg/ml, 5-FC 512 µg/ml, FLCZ 512 µg/ml or MCZ 256 µg/ml. By the use of the prepared drug the two fold dilution series was prepared in an appropriate concentration range with DMSO or water, and separately infused by 25 µl/well and formed into the dry and solid phase under vacuum (13.3–26.6 Pa) for 24 hrs. After the solid phase formation of the antifungal, the color reagent consisting of WST-8 0.7 mM, 1-methoxy PMS 3.5 µM, potassium ferricyanide 0.5 mM and potassium ferrocyanide 0.5 mM was separately infused by 20 µl/well and formed into the dry and solid phase under vacuum for 24 hrs.

C. Testing Method

1) Turbidity Method (comparative example)

For the comparison was used the 1.2% glucose MOPS buffered RPMI 1640medium and it was carried out according to the proposed method of Japanese Society for Medical Mycology (the microdilution method of 0.2 ml incubation system).

2) Microplate Method (the method of the invention)

(1) Preparation of inoculated fungal suspension and incubation

By using the colony within 24 hrs. in the incubation was prepared the fungal suspension with the sterile saline 5 ml. The fungal suspension corresponding to McFarland # 0.5 was prepared by measuring the absorbancy at the wave length of 530 nm. 0.1 ml of the prepared fungal suspension was taken by the micropipette, added to 0.9 ml of the 1.2% glucose MOPS buffered PRMI 1640 medium, and stirred thoroughly by the vortex-mixer, and then 0.1 ml of this was taken by the micropipette, added to 20 ml of the 1.204 glucose MOPS buffered PRMI 1640 medium, and stirred thoroughly by the vortex-mixer to prepare the replicated fungal suspension ($0.5 \times 10^3$–$2.5 \times 10^3$ cfu/ml). The replicated fungal suspension prepared was separately inoculated by 200 µl into each well of the microplate dryly fixed with the drug having the concentration gradient of the two fold dilution prepared in the above B. After lidding the plate the aerobic culture was done at 35±1° C. The absorbancy at 630 nm of the growth control (the testing fungal strains were incubated in the well wherein the antifungal agents and the color reagent was not formed into the solid phase) after the 24 hrs. incubation was measured. In the case that the measured absorbancy showed not less than 0.2, this point was made the end point, and in the case that the absorbancy was less than 0.2, the absorbancy after 48 hrs. was measured.

(2) Reading Method

After stirring the microplate under shaking for 1 min., the absorbency of the dominant wave length 450 nm and the complementary wavelength 630 nm was measured, and the reading was carried out by the following method.

1. The minimum concentration showing the absorbancy in AMPH equal to or less than that in the negative control was made the minimum growth inhibition concentration (MIC).

2. The 80% growth inhibition concentration (IC 80) was read in 5-Fc, FLCZ and MCZ. The drug concentration of the well showing the absorbancy equal to or less than the absorbency obtained by the following equation was made MIC.

$$(IC80 = (positive\ control - negative\ control) \times 0.2 + negative\ control)$$

D. Results

On repeatedly testing the six ATCC standard fungal strains, the results by the turbidity method and the microplate method of the invention were summarized in Table 3 and Table 4. In the turbidity method, 101 times (59.1%) among the total 171 times were within the MIC acceptable range proposed by the NCCLS M27-A. As for AMPH the rate of concordance was low, though the reproducibility of MIC was high, and all were distributed within 3 sigmas. In the method of the invention, 131 times (76.6%) among the total 71 times were within the MIC acceptable range proposed by the NCCLS M27-A, showing the rate of concordance higher than the results of the turbidity method carried out at the same time.

The drug susceptibility testing can be carried out simply and in a high reproducibility by the trace liquid dilution method using the microplate of the invention. Therefore, the microplate in which a drug and a color reagent are formed into a solid phase, and the kit product consisting of the microplate and a medium for a cell growth in the present invention are extremely high in the utility value as those for a clinical examination.

| Name of fungal strain | Name of drug | reference range (µg/ml) | Turbidity method | Method of the invention |
|---|---|---|---|---|
| C. parapsilosis ATCC 22019 | AMPH | 0.25–1.0 | 0.06–0.25 | 0.12–1.0 |
|  | 5-FC | 0.12–0.5 | 0.12–0.5 | 0.12–0.5 |
|  | FLCZ | 2.0–8.0 | 1.0–2.0 | 2.0–4.0 |
|  | MCZ |  | 0.25–0.5 | 0.5–1.0 |

-continued

| Name of fungal strain | Name of drug | reference range (μg/ml) | Turbidity method | Method of the invention |
|---|---|---|---|---|
| C. krusei ATCC 6258 | AMPH | 0.5–2.0 | 0.12–0.5 | 0.25–0.5 |
| | 5-FC | 4.0–16 | 8.0–16 | 8.0–16 |
| | FLCZ | 16–64 | 8.0–64 | 16–64 |
| | MCZ | | 0.25–1.0 | 0.25–1.0 |
| C. albicans ATCC 90028 | AMPH | 0.5–2.0 | 0.12–0.5 | 0.12–0.5 |
| | 5-FC | 0.5–2.0 | 0.25–2.0 | 0.25–1.0 |
| | FLCZ | 0.25–1.0 | 0.12–0.25 | 0.25–1.0 |
| | MCZ | | 0.06–0.12 | 0.06–0.12 |
| C. albicans ATCC 24433 | AMPH | 0.25–1.0 | 0.12–0.5 | 0.12–0.5 |
| | 5-FC | 1.0–4.0 | 0.5–2.0 | 0.5–2.0 |
| | FLCZ | 0.25–1.0 | 0.12–1.0 | 0.25–8.0 |
| | MCZ | | 0.06–0.5 | 0.06–1.0 |
| C. parapsilosis ATCC 90018 | AMPH | 0.5–2.0 | 0.12–0.25 | 0.12–0.25 |
| | 5-FC | 0.12–0.25 | 0.12 | 0.12 |
| | FLCZ | 0.25–1.0 | 0.5 | 0.5–2.0 |
| | MCZ | | 0.06–0.25 | 0.12–0.5 |
| C. tropicalis ATCC 750 | AMPH | 0.5–2.0 | 0.12–0.5 | 0.12–0.5 |
| | 5-FC | 0.12–0.25 | 0.12 | 0.12 |
| | FLCZ | 1.0–4.0 | 0.5–1.0 | 0.5–2.0 |
| | MCZ | | 0.12–1.0 | 0.25–2.0 |

| | | Turbidity method *2 | | | | | | | Method of the invention | | | | | |
|---|---|---|---|---|---|---|---|---|---|---|---|---|---|---|
| Name of fungal strain | Name of drug | −3 | −2 | −1 | ±0 (Rate of concordance) | +1 | +2 | +3 | −3 | −2 | −1 | ±0 (Rate of concordance) | +1 | +2 | +3 |
| C. parapsilosis ATCC 22019 (n = 10)*1 | AMP H 5-FC FLCZ | | 2 | 4 4 | 4 (40%) 10 (100%) 6 (60%) | | | | | | 2 | 8 (80%) 10 (100%) 10 (100%) | | | |
| C. krusei ATCC 6258 (n = 10) | AMP H 5-FC FLCZ | | 2 | 6 1 | 2 (20%) 10 (100%) 9 (90%) | | | | | | 1 | 9 (90%) 10 (100%) 10 (100%) | | | |
| C. albicans ATCC 90028 (n = 10) | AMP H 5-FC FLCZ | 7 | 2 | 5 5 | 1 (10%) 5 (50%) 5 (50%) | | | | 3 | 5 | 1 | 2 (20%) 9 (90%) 10 (100%) | | | |
| C. albicans ATCC 24433 (n = 10) | AMP H 5-FC FLCZ | | 3 | 4 1 3 | 6 (60%) 6 (60%) 7 (70%) | | | | | 2 3 | | 8 (80%) 7 (70%) 6 (60%) | 1 | 3 | |
| C. parapsilosis ATCC 90018 (n = 7) | AMP H 5-FC FLCZ | | 6 | 1 | 0 (0%) 7 (100%) 7 (100%) | | | | | 2 | 5 | 0 (0%) 7 (100%) 6 (86%) | 1 | | |
| C. tropicalis ATCC 750 (n = 10) | AMP H 5-FC FLCZ | | 5 | 3 6 | 2 (20%) 10 (100%) 4 (40%) | | | | | 5 | 4 | 1 (10%) 10 (100%) 8 (80%) | | | |

*1: The within ( ) is the number of measurements.
*2: The within of the reference range of NCCLSM-27A was made ±0, susceptibility 1 sigma as ±1, susceptibility 2 sigma as ±2, susceptibility 3 simga ±3.

What is claimed is:

1. A microplate for drug susceptibility testing, the microplate having a plurality of wells having a solid phase, the solid phase comprising (i) a drug, (ii) a color reagent, (iii) potassium ferricyanide, and (iv) potassium ferrocyanide, wherein the solid phase is formed by:

(a) dissolving the drug in dimethyl sulfoxide to form a solution;

(b) infusing a fixed amount of the solution formed in step (a) into each well of the microplate;

(c) vacuum drying the solution in each well to form a solid;

(d) infusing the color reagent, potassium ferricyanide, and potassium ferrocyanide into each well on top of the solid formed in step (c); and (e) vacuum drying each well from step (d) to yield the solid phase.

2. The microplate of claim 1, wherein the color reagent contains a tetrazolium salt and 1-methoxy-5-methylphenazinium methylsulfate.

3. The microplate of claim 1, wherein the drug is an antifungal agent.

4. The microplate of claim 3, wherein the antifungal is selected from the group consisting of amphotericin B, flucytosine, fluconazole, miconazole, and itraconazole.

* * * * *